US011719626B2

(12) United States Patent
Hosseini

(10) Patent No.: US 11,719,626 B2
(45) Date of Patent: Aug. 8, 2023

(54) ULTRA-MINIATURE SPATIAL HETERODYNE SPECTROMETER

(71) Applicant: California Institute of Technology, Pasadena, CA (US)

(72) Inventor: Seyedeh Sona Hosseini, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/218,130

(22) Filed: Mar. 30, 2021

(65) Prior Publication Data

US 2021/0302305 A1 Sep. 30, 2021

Related U.S. Application Data

(60) Provisional application No. 63/002,034, filed on Mar. 30, 2020.

(51) Int. Cl.
*G01N 33/18* (2006.01)
*G01N 21/25* (2006.01)
*G01J 3/28* (2006.01)
*G01N 33/49* (2006.01)
*G01N 33/24* (2006.01)
*G01N 33/483* (2006.01)

(52) U.S. Cl.
CPC .......... *G01N 21/255* (2013.01); *G01J 3/2823* (2013.01); *G01N 33/18* (2013.01); *G01N 33/24* (2013.01); *G01N 33/4833* (2013.01); *G01N 33/49* (2013.01)

(58) Field of Classification Search
CPC .......... G01J 3/2823; G01J 3/45; G01N 21/255
See application file for complete search history.

(56) References Cited

U.S. PATENT DOCUMENTS

2014/0247447 A1\* 9/2014 Angel .................. G01N 21/65
356/301
2021/0003450 A1\* 1/2021 Hunter .................. G01J 3/189

FOREIGN PATENT DOCUMENTS

BY 8490 U \* 8/2012
CN 106918393 A \* 7/2017
(Continued)

OTHER PUBLICATIONS

Jun Qiu,"Broadband transmission Raman measurements using a field-widened spatial heterodyne Raman spectrometer with mosaic grating structure", Aug. 23, 2018 (Year: 2018).\*
(Continued)

*Primary Examiner* — Maurice C Smith

(57) ABSTRACT

Ultra-miniature spatial heterodyne spectrometers (SHSs) are presented. Ultra-miniature SHSs in accordance with the invention, comprise a beam-splitter and gratings configured to generate a fringe pattern for spectroscopic detection. Many embodiments include input optics and a sensor and are configured in a way to omit collimating optics and imaging optics from the SHS. Compared to conventional SHSs known in the art, the present invention enables fewer parts, significantly smaller and lighter SHSs, are more efficient and robust, and require less maintenance. Many embodiments are field-deployable, in that such embodiments can be deployed for hand held use in real-world or remote activities outside of research or diagnostic facilities.

22 Claims, 5 Drawing Sheets

(56) References Cited

FOREIGN PATENT DOCUMENTS

CN           105300521 B * 11/2019
WO    WO-2021096588 A1 * 5/2021

OTHER PUBLICATIONS

David Kruse "LOWSPEC Spectrometer—Part 1—3D Printing", https://www.youtube.com/watch?v=Wac5asXagEQ, 2019 (Year: 2019).*
Hosseini, Sona, "Khayyam: a tunable spatial heterodyne spectrometer for observing diffuse emission line targets", 2012 (Year: 2012).*
Martin Kaufmann, "A highly miniaturized satellite payload based on a spatial heterodyne spectrometer for atmospheric temperature measurements in the mesosphere and lower thermosphere", Dec. 2017 (Year: 2017).*
Canon USA, "Canon 120MXS 120MP CMOS Sensor", Mar. 29, 2018 https://www.youtube.com/watch?v=40yruxcr-yQ (Year: 2018).*
Olivia R. Dawson,"Tunable, all-reflective spatial heterodyne spectrometer for broadband spectral line studies in the visible and near-ultraviolet", Mar. 13, 2009 (Year: 2009).*
Christoph R. Englert,"Correction of Phase Distortion in Spatial Heterodyne Spectroscopy", 2005 Optical Society of America (Year: 2005).*
John M. Harlander,"First results from an all-reflection spatial heterodyne spectrometer with broad spectral coverage", 2010 (Year: 2010).*
Harris et al., "Applications of reflective spatial heterodyne spectroscopy to UV exploration in the Solar System", Proceedings of SPIE vol. 5488, UV and Gamma-Ray Space Telescope Systems, Oct. 11, 2004, pp. 886-897.

* cited by examiner

ULTRA-MINIATURE SPATIAL HETERODYNE SPECTROMETER

CROSS-REFERENCE TO RELATED APPLICATIONS

The current application claims priority to U.S. Provisional Patent Application No. 63/002,034, entitled "Miniature Spatial Heterodyne Spectrometer" to Seyedeh Sona Hosseini, filed Mar. 30, 2020, the disclosure of which is hereby incorporated by reference in its entirety.

STATEMENT OF FEDERAL FUNDING

This invention was made with government support under Grant No. 80NM0018D0004 awarded by NASA (JPL). The government has certain rights in the invention.

FIELD OF THE INVENTION

The present disclosure is directed to spatial heterodyne spectrometers, particularly to devices comprising spatial heterodyne spectrometers with significantly reduced size.

BACKGROUND OF THE INVENTION

Low-resolution spectroscopy allows the study of basic parameters like composition, distribution, intensity, and energy distribution. In contrast, high-resolution spectroscopy can reveal additional information about the physical characteristics of a source, such as a velocity, temperature, pressure, isotopic signatures, etc. High-resolution spectroscopy carries more information than low-resolution spectroscopy. Yet, the cost of the added information must be balanced against other restrictive factors, most importantly size and mass of the instrument and the maintenance of optics' alignment.

Spectroscopy targets cover a vast range of sizes and environments that present a challenge to spectroscopic observers. Current spectroscopic techniques fall short in addressing high resolving power (R) observations at wide field-of-view (FOV) and high throughput. Most existing conventional instrumental designs lose their sensitivity by going to lower resolution and lower throughput. This type of sensitivity trade-off presents fewer challenges for point sources or very small sources, but it restricts the spectroscopic investigation of the extended sources. For example, in astronomy, the velocity of a galaxy that is moving with the relative velocity of 600 km/sec can be detected with an instrument with an R of ~500. By contrast, the velocity distributions in comets cover a range of 1-100 km/s, which requires R up to 100,000 to detect the corresponding Doppler shift. In addition, the faintness and angular extent of many of the target emissions and the volume limitations of remote probes and small spacecraft restrict the opportunities for incorporating a high spectral resolution capability and requires a need for high-throughput, compact—for space probe applications as well as field commercial applications—and high-resolution spectral sensors.

Many high-resolution spectrometers are large, bulky, and require to be paired with large input optics (such as large telescope or large microscopes) or have an excess mass that makes them insufficient to be deployed in the field such as in space and/or on robotic platforms. As such, a need exists in the art for spectrometers with a small form factor to deploy in space or on planetary bodies, where reduced size and mass are essential features for use.

SUMMARY OF THE INVENTION

This summary is meant to provide examples and is not intended to be limiting of the scope of the invention in any way. For example, any feature included in an example of this summary is not required by the claims unless the claims explicitly recite the feature.

In one embodiment, a field-deployable device for performing spectroscopy includes an aperture, input optics, a spatial heterodyne spectrometer (SHS) including a beam-splitter, a first grating, and a second grating, and a spectroscopy sensor configured to acquire a fringe pattern generated by the SHS, where the aperture, the input optics, the SHS, and the spectroscopy sensor are in optical alignment, such that incoming light passes through the aperture into the input optics, the input optics are configured to direct light to the SHS, the beam-splitter, the first grating, and the second grating form a 90° angle with the beam-splitter at the vertex of the angle; and wherein the beam-splitter is configured to split the incoming light to the first grating and the second grating, and a position of the aperture, a position of the first grating, and a position of the second grating are configured such that a fringe localization pattern is located proximal to the aperture.

In a further embodiment, the field-deployable device further includes a first field widened prism and a second field widened prism, where the first field widened prism is located between the beam-splitter and the first grating and the second field widened prism is located between the beam-splitter and the second grating.

In another embodiment, a position of the first field widened prism and a position of the second field widened prism are configured such that the fringe localization pattern is located proximal to the aperture.

In a still further embodiment, the first field widened prism forms a first angle $\alpha$ with an edge of the beam-splitter and an edge of the first field widened prism proximal to the beam-splitter, the second field widened prism forms a second angle $\alpha$ with an edge of the beam-splitter and an edge of the second field widened prism proximal to the beam-splitter, and the first angle $\alpha$ and the second angle $\alpha$ are configured such that the fringe localization pattern is located proximal to the aperture.

In still another embodiment, the first grating is tilted to form a first angle $\beta$ between the first grating and a path of light directed toward the first grating, the second grating is tilted to form a second angle $\beta$ between the second grating and a path of light directed toward the second grating, and the first angle $\beta$ and the second angle $\beta$ are configured such that the fringe localization pattern is located proximal to the aperture.

In a yet further embodiment, the aperture, the input optics, the SHS, and the sensor are housed in a frame and barrel assembly.

In yet another embodiment, the frame and barrel assembly are 3D printed.

In a further embodiment again, the field-deployable device further includes a bandpass filter and an imaging sensor; where the incoming light passes intercepts the bandpass filter, wherein specific wavelengths of the intercepted light are deflected toward the input optics; wherein the remaining wavelengths of light pass through the bandpass filter and impinge on the imaging sensor.

In another embodiment again, the aperture, the input optics, the SHS, the sensor, the bandpass filter, and the imaging sensor are housed in a frame and barrel assembly.

In a further additional embodiment, the frame and barrel assembly are 3D printed.

In another additional embodiment, the field-deployable device has a mass of less than 500 grams.

In a still yet further embodiment, the input optics are selected from a telescope, a microscope, and a coupled optical fiber system.

In still yet another embodiment, a method of using a field-deployable spectroscopy device includes obtaining a light emission from a sample, where the light emission passes through input optics into an SHS to image a fringe pattern on a sensor, and analyzing the fringe pattern to identify a component within the sample.

In a still further embodiment again, the method further includes obtaining a sample.

In still another embodiment again, the sample is a biological sample.

In a still further additional embodiment, the biological sample is obtained from at least one of saliva, mucus, blood, urine, fecal, skin, and tissue.

In still another additional embodiment, the sample is an environmental sample selected from a water sample, soil sample, rock sample, air sample.

In a yet further embodiment again, the sample is obtained from a high-touch area.

In yet another embodiment again, the sample is a pharmaceutical.

In a yet further additional embodiment, the method further includes illuminating the sample.

The foregoing and other objects, features, and advantages of the disclosed technology will become more apparent from the following detailed description, which proceeds with reference to the accompanying figures.

BRIEF DESCRIPTION OF THE DRAWINGS

The description will be more fully understood with reference to the following figures and data, which are presented as exemplary embodiments of the disclosure and should not be construed as a complete recitation of the scope of the invention, wherein.

DETAILED DESCRIPTION OF THE INVENTION

Turning to the drawings, ultra-miniature spatial heterodyne spectrometers, their methods of use, and methods of their manufacture are provided. In various embodiments, the miniature spatial heterodyne spectrometer assemblies maintain a heterodyne condition such that for the heterodyne wavelength, or the tuned wavelength, there is no data in the form of fringes. However, for wavelengths other than the heterodyne wavelength but within the bandpass range, visible localized fringe patterns may be produced. In some such embodiments, the gratings within the spectrometer may be holographic, symmetric, non-blazed, sinusoidal, or triangular. In some other embodiments, the miniature spatial heterodyne spectrometers may incorporate field-widening elements, such as, for example, wedge prisms; other optical elements, such as mirrors, transmission gratings, or lenses. In still other embodiments, the miniature spatial heterodyne spectrometers may incorporate a coupled optical fiber system.

Recent autonomous robotic technological advances in space exploration enable the promise of exploring planetary bodies in situ and in the shortest time. However, the necessary science instrument payload technology combining high sensitivity with low mass and power is currently lacking. Many embodiments enable high precision spectra measurements onboard small robotic platforms (e.g., having less than 500 grams payload capacity). Due to the small size or form factor, additional embodiments allow for handheld operation. Numerous embodiments employ Spatial Heterodyne Spectrometry (SHS), an interferometric technique with no moving parts. SHS in accordance with various embodiments is suitable for obtaining high precision measurements from a targeted narrow wavelength range from diffused aperture filling targets. Because its wavelength range can be set to other species in other wavelengths from UV to near IR, various embodiments have widespread applications in the future, including multi-agent Solar System exploration missions and finding life elsewhere.

Technical Concept for Ultra-Miniature Spatial Heterodyne Spectrometers

Figure 1:
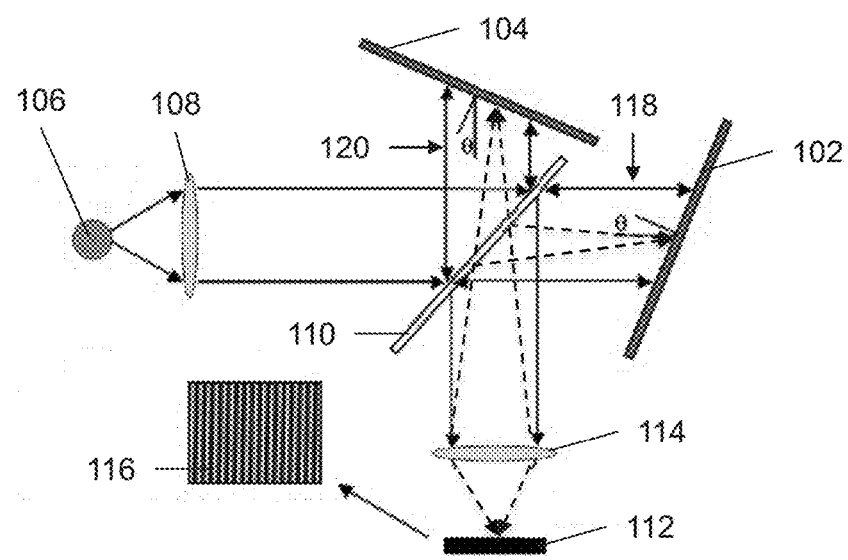
FIG. 1 illustrates a spatial heterodyne spectrometer (SHS), including collimating optics and imaging optics.

Turning to FIG. 1, the original spatial heterodyne spectrometer (SHS) configuration 100 is a Michelson design SHS (MSHS) in a Michelson interferometer configuration where reflection diffraction gratings replace the mirror in each interferometer arm. The Michelson Spatial Heterodyne Spectrometer (SHS) is a miniature interferometer that can observe targeted atomic and molecular spectral lines at high spectral resolution. An MSHS is generally tailored to a target wavelength region (UV to VIS) with a 2-dimensional (2D) solid-state array imaging sensor that produces records of the optical interference fringes, whose Fourier transform produces high-resolution spectra. With its high optical throughput (étendue) and wide field of view (FOV), it has a high sensitivity to weak or diffuse sources such as the ability to measure biomarkers, both organic and inorganic, minerals, water, and CO2 ice.

As illustrated in FIG. 1, the Michelson interferometer configuration in accordance with various embodiments possesses a centrally located beam-splitter 110 surrounded by reflection diffraction gratings 102, 104 forming a 90° angle, such that beam-splitter 110 is the vertex of the 90° angle. In several embodiments, each reflection diffraction grating 102, 104 is tilted at an angle α In many embodiments, light emitted from a field of view 106 is collimated via a collimator 108, such as a collimating lens, mirror, or other optical elements capable of collimating light. Collimated light intercepts the beam-splitter 110 90° from one of the gratings 102, 104. The beam-splitter 110 directs collimated light to gratings 102, 104. One or both gratings 102, 104 can be moved via an interferometer arm. For example, grating 102 can be moved along an axis parallel to the collimated light from collimator 108 to beam-splitter 110, while grating 104 can be moved along an axis perpendicular to the collimated light from collimator 108 to beam-splitter 110. Gratings 102, 104 diffract light back toward beam-splitter 110, where the diffracted light is recombined and directed toward a detector 112, such as a camera or other sensor. Some embodiments include additional optics 114 to focus recombined light to detector 112. Light collimated into the system emerges as crossed wavefronts, which interfere creates a Fizeau fringe pattern 116.

The FOV is significant for SHS because it increases the étendue of the instrument, the capability of an optical system to accept and gather light ($É=FOV \times A_{eff}$; where $A_{eff}$ is the collecting area). Provided the source is extended, and aperture-filling, the FOV of the SHS can fill the same role that a large input optics does for a grating spectrometer. The measure of étendue is widely used to express the sensitivity of an optical instrument. To date, solutions to use outside FOV rays to increase the size of FOV in SHS systems have not been demonstrated.

Field-widening usually involves adding at least one optical element into the SHS assembly with the goal of making beams from outside the FOV appear to be within the FOV limits, widening the instrument's FOV. The instrument's throughput will be increased (without a significant increase in input optical system size), leading to higher sensitivity that provides faster and better data gathering while retaining the advantages of the conventional SHS. In short, field-widening, if done successfully, will enable a smaller, lighter SHS that can be very useful for applications requiring minimal volume and weight loadings (e.g., space exploration, portable commercial applications).

In several embodiments, the SHS is field-widened by inserting prisms at positions 118, 120. Such prisms can be wedge prisms so that, when gratings 102, 104 are viewed from the output, they appear rotated to be co-linear. Field-widening can increase the SHS etendue by a couple of orders of magnitude over the basic configuration, making it very useful for diffuse-source observations.

Field-Deployable SHS Devices

Figure 2A:
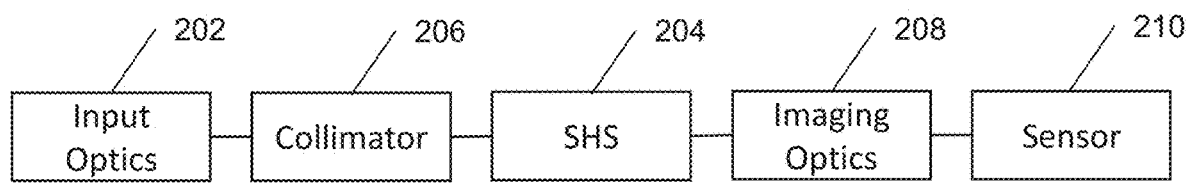
FIG. 2A illustrates a schematic representation of an SHS system.

Many embodiments are directed to devices comprising and SHS that can be deployed for use in real-world, or "field," settings, such as astronomy, ophthalmology, virology, or any other field where elucidating spectral emissions will be of benefit in understanding underlying chemistry or conditions. In many embodiments, the field-deployable devices allow for remote activities outside of research or diagnostic facilities. Turning to FIG. 2A, traditional means of utilizing SHSs include utilizing input optics 202 to bring light into an SHS 204. However, in these traditional implementations, a collimator 206 is necessary to focus light from the input optics 202 into the SHS 204. Additionally, imaging optics 208 are further necessary to focus the output light from the SHS 204 to a sensor 210. However, the introduction of each component (input optics 202; collimator 206, imaging optics 208; SHS, 204; and sensor 210) increases the weight and size of any resultant device. Additionally, each component's addition increases the number of components that must be aligned and increases the likelihood of misalignments due to vibrations, thermal expansion/contraction, or any other stressors that can affect the performance of an SHS when deployed. Additionally, current technology only allows miniaturization to the size of approximately 1-2 shoeboxes in size (1 shoebox has dimensions of approximately 35×25×13 centimeters)—a size commonly referred to as "backpack" sized.

Figure 2B:
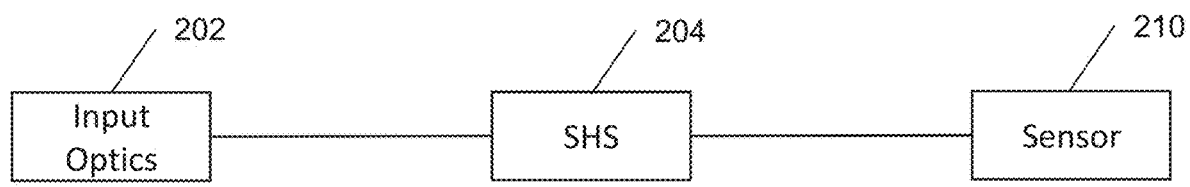
FIG. 2B illustrates a schematic representation of an SHS system in accordance with various embodiments of the invention.

Many embodiments compensate for the shortcomings of traditionally deployed SHSs by assembling the input optics 202, SHS 204, and sensor 210 at specific positions such that the collimator 206 and imaging optics 208 are omitted, such as illustrated in FIG. 2B. The ability to omit the collimator 206 and imaging optics 208 arises from the physics of light transmission and Fourier transform that allows for specific placement and alignment of input optics 202, SHS 204, and sensor 210 to obviate any need for the collimator 206 and imaging optics 208.

Such embodiments are able to omit the collimator 206 and imaging optics 208 due to the location of the fringe localization plane (FLP). In traditional SHS, fringes are made to appear in a region of space where the interference pattern can be observed in its best contrast which depends on the properties of the source and the geometry of the instrument. For SHSs observing extended sources, the fringes have high visibility over only a certain surface in the observation space that can vary from a plane to an odd shape, or can be localized in infinity. The fringe localization plane (FLP) in Michelson SHS instruments is often placed on the surface of the grating which then is imaged on the sensor by the imaging optics. In contrast, many embodiments relocate the FLP proximal to the input aperture. By relocating the FLP proximal to the input aperture, the FLP can be imaged on the sensor without the need for imaging optics 208.

In various embodiments, the input optics 202 are any components to move light. In certain embodiments, the input optics also change the magnification of the light. Depending on the specific use, various embodiments utilize one or more of a telescope, microscope, or optical fiber system as the input optics 202.

Additionally, various embodiments utilize a sensor with small pixel size, such as a cell phone camera. Many embodiments utilize monochrome cell phone cameras or cell phone cameras with lenses and filters removed to allow for imaging of fringe patterns with high resolution while maintaining a small form factor.

Advantages of these embodiments allow for ultra-miniaturization of SHS devices, include increased tolerances, reduced size, mass, volume, cost, and maintenance due to fewer components. Furthermore, alignment is more secure, as fewer components are susceptible to shock and thermal expansion/contraction. Additionally, many embodiments can be miniaturized to be handheld or deployable on small robots, making them suitable for deployment on spacecraft or planetary landers (e.g., mars rovers) for data collection/analysis. Additionally, fewer components make numerous embodiments amenable to automated assembly for mass development.

Figure 3:
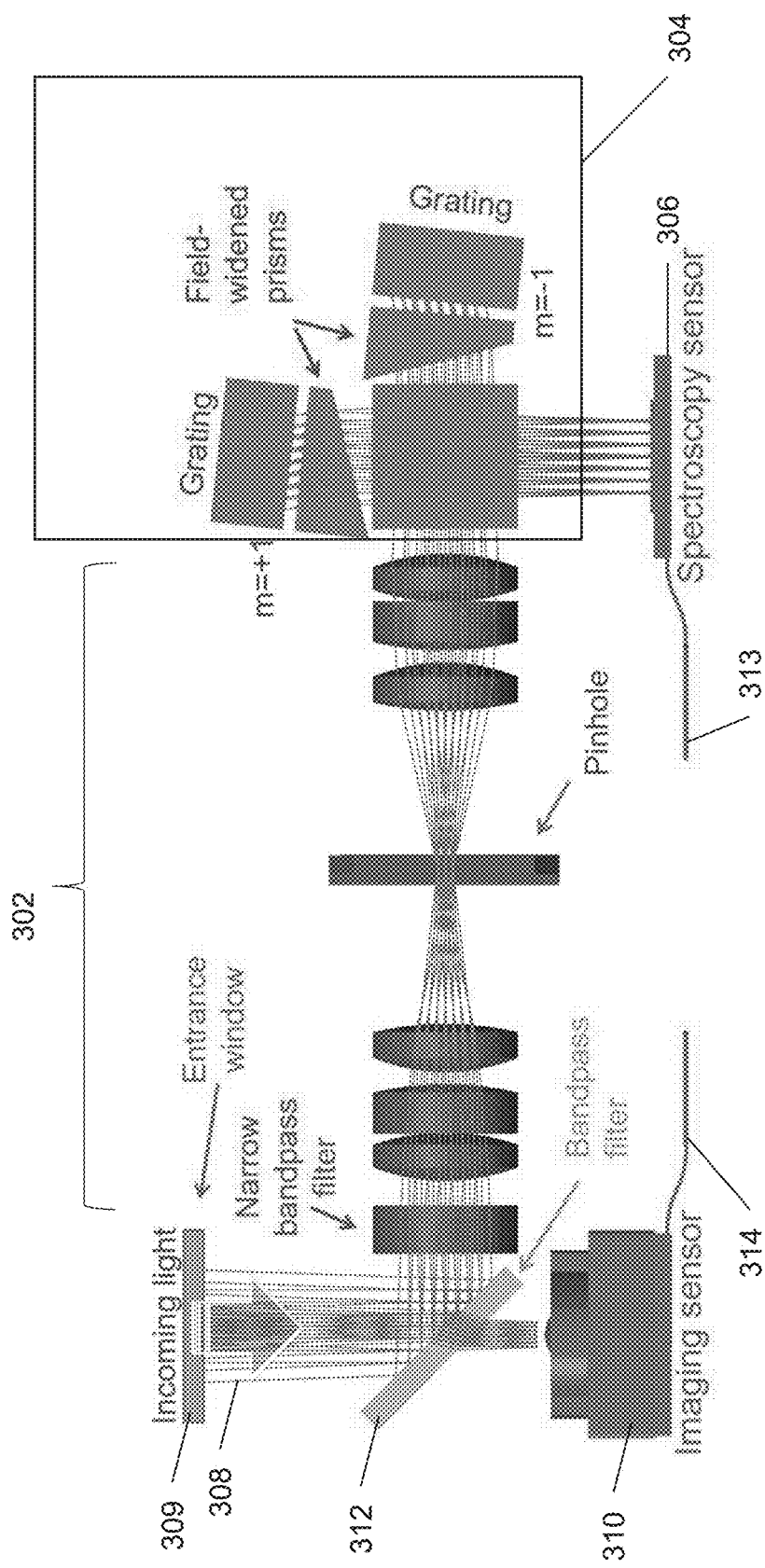
FIG. 3 illustrates the optical concept of a field-deployable SHS system in accordance with various embodiments of the invention.

FIG. 3 illustrates an exemplary embodiment of a field-deployable SHS in accordance with various embodiments. FIG. 3 illustrates input optics 302, SHS 304, and spectroscopy sensor 306 in optical alignment in accordance with many embodiments. In such embodiments, incoming light 308 through an entrance window 309 and is routed through input optics 302 and SHS 304 to the spectroscopy sensor 306. As illustrated, various embodiments of the input optics 302 include various optical components for the operation of the input optics 302, including one or more of a narrow bandpass filter, pinhole, lenses, prisms, and/or any other optical component configured to direct light toward the SHS 304.

In many embodiments, the SHS 304 includes various components, such as described above, including one or more of a beam-splitter, gratings, and/or field-widening prisms. As noted above and illustrated within FIG. 3, light exiting SHS 304 intercepts a spectroscopy sensor 306 configured to detect fringe patterns generated by the SHS 304.

Further embodiments include an imaging sensor 310 to allow for simultaneous imaging and spectroscopy. In such embodiments, incoming light 308 can intercept a bandpass filter 312 where specific wavelengths of light for spectroscopy are deflected toward the input optics 302, while the remaining wavelengths of light pass through the bandpass filter 312 toward the imaging sensor 310.

Further embodiments include electronic connectors 313, 314 for the spectroscopy sensor 306 and imaging sensor 310, respectively. Such electronic connectors allow field-deployable devices to interact with computing devices for analysis, image overlay, data transmission, or other relevant computational interaction or control of such embodiments.

Figure 4:
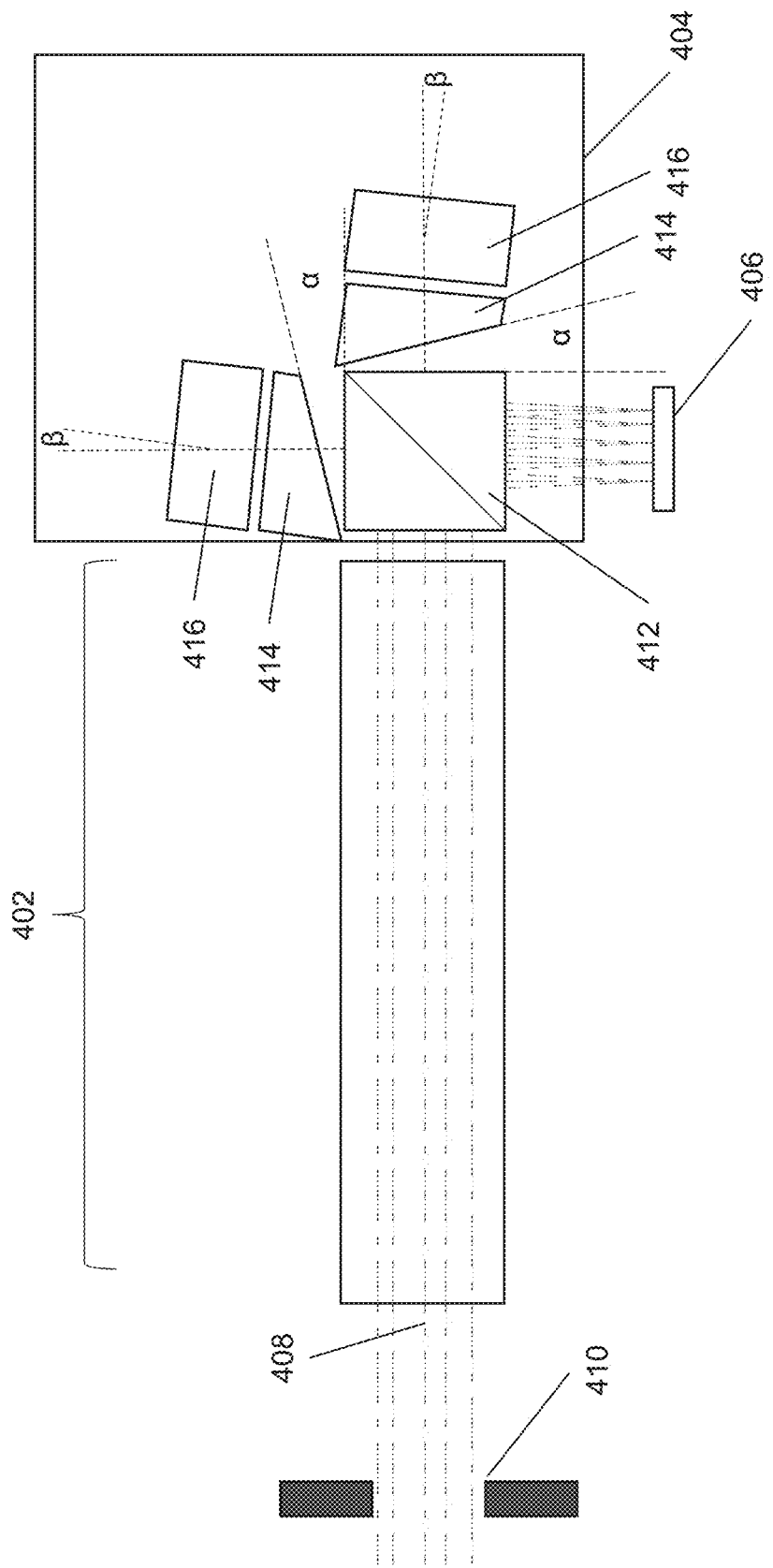
FIG. 4 illustrates a schematic of a field-deployable SHS system in accordance with various embodiments of the invention.

As illustrated in FIG. 4, many embodiments include input optics 402, an SHS 404, and a sensor 406 in optical alignment. Similar to FIG. 3, incoming light 408 passes through input optics 402, before reaching SHS 404. SHSs in accordance with various embodiments include a beam-splitter 412, prisms 414, and gratings 416. Once light 408 reaches the SHS 404, beam-splitter 412 directs light through prisms 414 toward gratings 416, where light is diffracted back toward beam-splitter 412, where light 408 is recombined, to form fringe patterns on sensor 406.

As noted above, many embodiments of a field-deployable SHS are able to omit or exclude at least one of collimating optics (e.g., optics between a input optics and an SHS) and imaging optics (e.g., optics between the SHS and an spectroscopy sensor). Embodiments are able to omit such optics by configuring the placement of various components such that the fringe localization plane is proximal to an aperture 410. Such components include one or more of an aperture 410, prisms 414, and gratings 416. In particular, various embodiments alter angles between certain components, such as prisms 414 and gratings 416, and/or alter the position of aperture 410. Some embodiments create an angle α between the beam-splitter 412 and prisms 414, such that angle α describes an angle created between an edge of beam-splitter 412 and a proximal edge of a prism. Additional embodiments comprise an angle β formed between the beam-splitter 412 and gratings 416, such that angle β describes an angle of tilt of a grating from an axis running parallel to a path of light directed toward that grating from beam-splitter 412.

Figure 5:
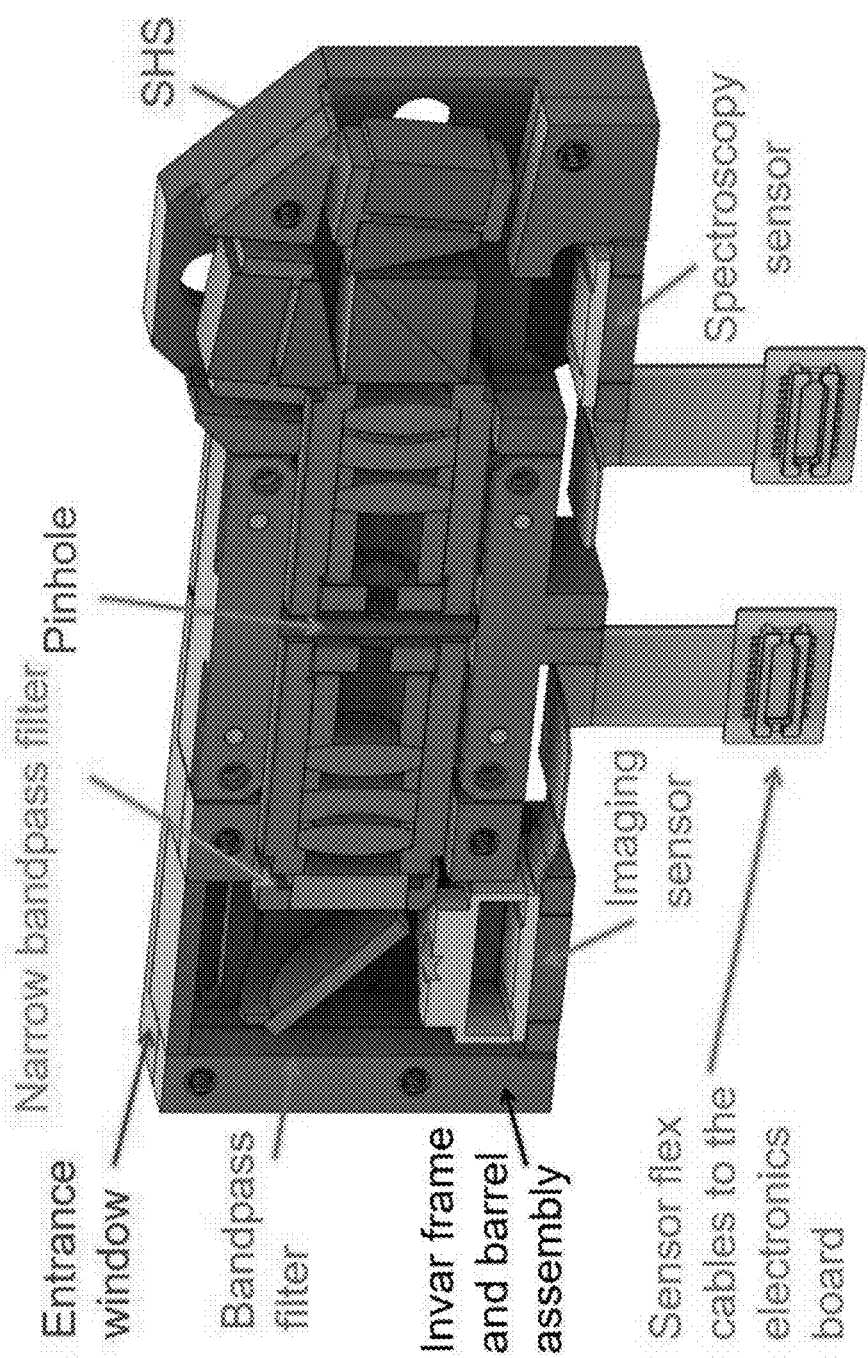
FIG. 5 illustrates an exemplary embodiment of a field-deployable SHS system form factor in accordance with various embodiments of the invention.

FIG. 5 illustrates an exemplary embodiment of field-deployable SHS device comprising a housing assembly. In many embodiments, the housing comprises a frame and barrel assembly, which can be 3D printed or precision machined to hold various components or features, such as a input optics, bandpass filters, SHS, sensors/detectors, etc. Such embodiments are able to reduce the form factor to approximately 160 grams and have dimensions of approximately 24×10×55 mm, making them suitable for handheld use, space deployment, or other uses where small form factors are preferable for field use. Table 1 lists various characteristics of the exemplary embodiment of FIG. 5. With the small form factor, many embodiments are capable of being handheld. Additionally, field-deployable SHS devices in accordance with many embodiments, are configurable with a variety of species within a very narrow spectral bandpass anywhere from near ultraviolet (UV) to infrared (IR) wavelength region.

Uses of Field-Deployable SHS Devices

It should be noted that there are many different types of spectroscopy, and various embodiments can be used in many types of spectroscopy for chemical analysis, including atomic spectroscopy, ultraviolet, and visible spectroscopy, infrared spectroscopy, fluorescence spectroscopy, and Raman spectroscopy. Various embodiments can be deployed for chemical analysis, while additional embodiments can be utilized for diagnostic screening or other implementations, where spectroscopy may suitable or for analysis or identification of underlying components or specimens.

Figure 6A:
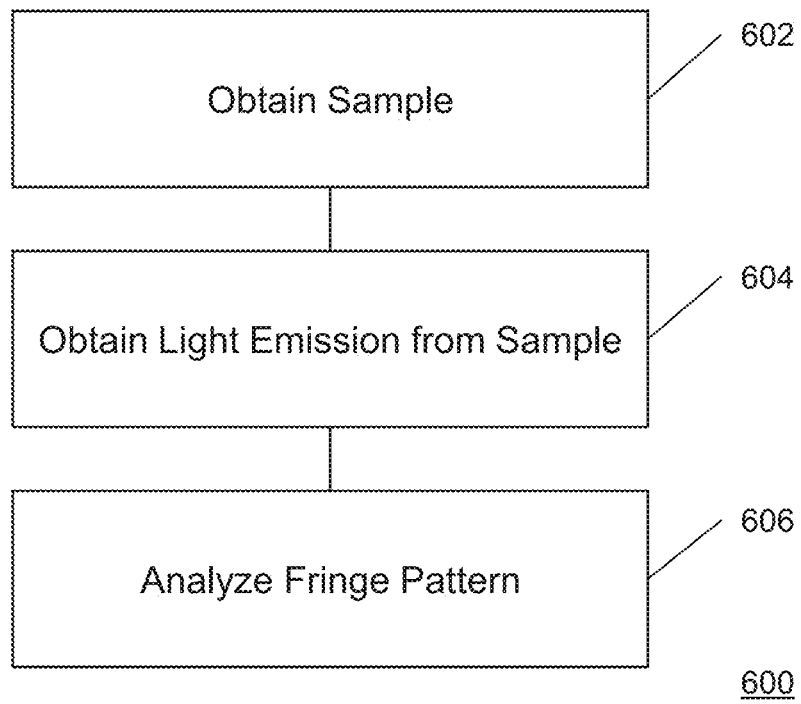
FIG. 6A illustrates a method for using a field-deployable SHS system in accordance with various embodiments of the invention.

Turning to FIG. 6A, a method 600 of using a field-deployable SHS device in accordance with many embodiments is illustrated. At 602, many embodiments obtain a sample. In various embodiments, the sample is organic, inorganic, biologic, or any other sample of interest. Some embodiments obtain a biological sample from an individual, such as saliva, mucus, blood, urine, fecal, skin, tissue, breath (e.g., exhaled breath) or other biological samples. Certain embodiments obtain an environmental sample, such as from a body of water (e.g., lake, river, stream, etc.), soil sample, rock sample, air sample, and/or another environmental sample. Various embodiments obtain samples from areas of human use, such as doorknobs, toilet handles, toilet seats, airplane seats (e.g., armrests, tray tables, etc.), surgical suites, hospital rooms, and/or any other high-touch area. Further embodiments obtain agricultural samples, such as leaves, sepals, petals, branches, canopy, or other type of agricultural sample, where water status (e.g., draught stress), pest or disease infection, or any other relevant feature can be monitored. Some embodiments obtain samples from chemical batches, including pharmaceutical batches, to test for purity or contamination.

Figure 6B:
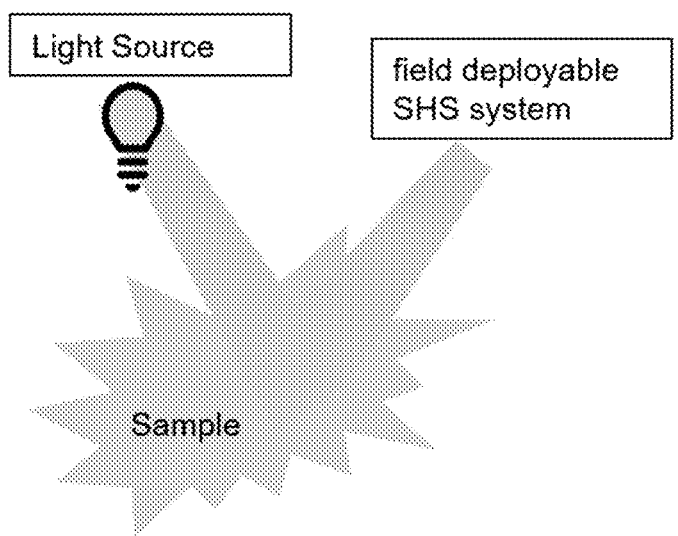
FIG. 6B illustrates an schematic of illuminating a sample in accordance with various embodiments of the invention.

At 604, many embodiments obtain a light emission from the sample. In certain embodiments, light emission is fluorescent signal emitted from the sample, while in other embodiments, light emission is reflection of a light from a sample (e.g. FIG. 6B). In certain embodiments, the light emission is obtained from ambient light being shined on the sample (e.g., from the sun), while certain embodiments illuminate the sample with a specific light source or wavelength of light, including for fluorescence spectroscopy, where specific wavelengths of light are used as an excitation wavelength for the sample. The obtained emission travels into a field-deployable SHS device as incoming light. As noted elsewhere herein, incoming light travels through input optics into an SHS and to a sensor, where a fringe pattern is imaged. Further embodiments include an imaging sensor to obtain a photographic image of the sample.

At 606, the fringe pattern is analyzed for one or more components in the sample. Such analysis may include comparisons to a database of standards. For example, the database could identify various chemical agents or compounds to identify one or more chemicals present within the sample, while other databases may provide spectra for microbes or viruses that could be present within a sample. As such, various embodiments could be deployed as field diagnostic devices for monitoring epidemics, pandemics, or other biological outbreaks that occur. While some embodiments can be deployed to check for purity or contamination within a batch of pharmaceuticals. Further embodiments can be deployed for exploration and analysis of soil, rock, or other environmental samples on other planetary bodies, such as Mars, Venus, the moon, or another planetary body. Various embodiments obtain databases from publicly available sources, while other embodiments generate novel databases over time.

It should be noted that the steps of method 600 may be performed in a different order or may be omitted depending on specific use of method 600. For example, certain embodiments may obtain a light emission 604 from an in situ sample, such as tree or field canopy or rock formation, thus omitting obtaining a sample 602. One of skill in the art will appreciate the ability to manipulate or augment certain features of method 600 to be suitable for a particular purpose.

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole and that variations in the components or steps of the present invention may be made within the spirit and scope of the invention. Accordingly, the present invention is not limited to the specific embodiments described herein but, rather, is defined by the scope of the appended claims.

TABLE 1

Characteristics of an exemplary embodiment

| | |
|---|---|
| Aperture | 5 mm |
| FOV | 4 × 4 degrees |
| Etendue | 6.01 × $10^{-7}$ str $m^2$ |
| Bandpass | 3067 to 3098 Å |
| Resolving Power | 36,000 |
| Spectral Resolution | 0.085 Å |
| Mass | ~160 grams |
| Power Ops | ~7 W |
| Operating Temperature | −40° C. to −10° C. |
| Non-Operating Temperature | −180° C. to +116° C. |
| Dimensions | ~23 × 10 × 55 mm |

What is claimed is:

1. A field-deployable device for performing spectroscopy comprising:
a spatial heterodyne spectrometer (SHS) comprising a beam-splitter, a first grating, and a second grating, wherein the beam-splitter, the first grating, and the second grating form a 90° angle with the beam-splitter at the vertex of the angle; and wherein the beam-splitter is configured to split the incoming light to the first grating and the second grating; and
a spectroscopy sensor configured to acquire a fringe pattern generated by the SHS, wherein the spectroscopy sensor comprises a solid-state array without lenses;
wherein the SHS and the spectroscopy sensor are in optical alignment, such that light exiting from the SHS directly passes to the spectroscopy sensor without optics configured to direct the light to the spectroscopy sensor.

2. The field-deployable device for performing spectroscopy of claim 1, further comprising a first field widened prism and a second field widened prism, wherein the first field widened prism is located between the beam-splitter and the first grating and the second field widened prism is located between the beam-splitter and the second grating.

3. The field-deployable device for performing spectroscopy of claim 1, wherein the SHS and the sensor are housed in a frame and barrel assembly; wherein the frame and barrel assembly forms an aperture; and wherein a position of the first grating, and a position of the second grating are configured such that a fringe localization pattern is located proximal to the aperture.

4. The field-deployable device for performing spectroscopy of claim 3, wherein a position of the first field widened prism and a position of the second field widened prism are configured such that the fringe localization pattern is located proximal to the aperture.

5. The field-deployable device for performing spectroscopy of claim 4, wherein the first field widened prism forms a first angle α with an edge of the beam-splitter and an edge of the first field widened prism proximal to the beam-splitter; wherein the second field widened prism forms a second angle α with an edge of the beam-splitter and an edge of the second field widened prism proximal to the beam-splitter, and wherein the first angle α and the second angle α are configured such that the fringe localization pattern is located proximal to the aperture.

6. The field-deployable device for performing spectroscopy of claim 3, wherein the first grating is tilted to form a first angle β between the first grating and a path of light directed toward the first grating; wherein the second grating is tilted to form a second angle β between the second grating and a path of light directed toward the second grating; and wherein the first angle β and the second angle β are configured such that the fringe localization pattern is located proximal to the aperture.

7. The field-deployable device for performing spectroscopy of claim 3, wherein the frame and barrel assembly are 3D printed.

8. The field-deployable device for performing spectroscopy of claim of claim 1 further comprising a bandpass filter and an imaging sensor; wherein the incoming light intercepts the bandpass filter, wherein specific wavelengths of the intercepted light are deflected toward the SHS, wherein the remaining wavelengths of light pass through the bandpass filter and impinge on the imaging sensor, and wherein light traversing the input optics passes to the SHS.

9. The field-deployable device for performing spectroscopy of claim 8, wherein the SHS, the spectroscopy sensor, the bandpass filter, and the imaging sensor are housed in a frame and barrel assembly; wherein the frame and barrel assembly forms an aperture; and wherein a position of the first grating, and a position of the second grating are configured such that a fringe localization pattern is located proximal to the aperture.

10. The field-deployable device for performing spectroscopy of claim 1, wherein the field-deployable device has a mass of less than 500 grams.

11. The field-deployable device for performing spectroscopy of claim 1, further comprising input optics that direct light to the SHS, wherein the input optics are selected from a telescope, a microscope, and a coupled optical fiber system.

12. The field-deployable device for performing spectroscopy of claim 1, wherein the solid-state array is without filters.

13. A method of using a field-deployable spectroscopy device comprising:

obtaining a light emission from a sample, wherein the light emission passes into a spatial heterodyne spectrometer (SHS) to image a fringe pattern on a spectroscopy sensor;

wherein the SHS, and the spectroscopy sensor are in optical alignment;

wherein the SHS comprises a beam-splitter, a first grating, and a second grating, wherein the beam-splitter, the first grating, and the second grating form a 90° angle with the beam-splitter at the vertex of the angle; and wherein the beam-splitter is configured to split the incoming light to the first grating and the second grating;

wherein the spectroscopy sensor is configured to acquire a fringe pattern generated by the SHS, wherein the spectroscopy sensor comprises a solid-state array without lenses; and wherein the SHS and the spectroscopy are in optical alignment, such that light exiting from the SHS directly passes to the spectroscopy sensor without optics configured to direct the light to the spectroscopy sensor; and analyzing the fringe pattern to identify a component within the sample.

14. The method of claim 13, further comprising obtaining a sample.

15. The method of claim 14, wherein the sample is a biological sample.

16. The method of claim 15, wherein the biological sample is obtained from at least one of saliva, mucus, blood, urine, fecal, skin, and tissue.

17. The method of claim 14, wherein the sample is an environmental sample selected from a water sample, soil sample, rock sample, air sample.

18. The method of claim 14, wherein the sample is obtained from a high-touch area.

19. The method of claim 14, wherein the sample is a pharmaceutical.

20. The method of claim 13, further comprising illuminating the sample.

21. The method of claim 13, wherein the SHS is configured for one or more of atomic spectroscopy, ultraviolet spectroscopy, visible spectroscopy, infrared spectroscopy, fluorescence spectroscopy, and Raman spectroscopy.

22. The method of claim 13, wherein the SHS is configured to identify one or more viruses in the sample.

* * * * *